United States Patent
Oosake

(10) Patent No.: US 12,205,244 B2
(45) Date of Patent: Jan. 21, 2025

(54) IMAGE PROCESSING APPARATUS, IMAGE PROCESSING METHOD, NON-TRANSITORY COMPUTER READABLE MEDIUM, AND ENDOSCOPE SYSTEM

(71) Applicant: FUJIFILM Corporation, Tokyo (JP)

(72) Inventor: Masaaki Oosake, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 29 days.

(21) Appl. No.: 18/454,777

(22) Filed: Aug. 23, 2023

(65) Prior Publication Data
US 2024/0070813 A1 Feb. 29, 2024

(30) Foreign Application Priority Data
Aug. 25, 2022 (JP) ................. 2022-134467

(51) Int. Cl.
*G06T 3/40* (2024.01)
*A61B 1/00* (2006.01)
*G06T 3/4046* (2024.01)
*G06T 3/4053* (2024.01)
*H04N 23/85* (2023.01)

(52) U.S. Cl.
CPC ........ *G06T 3/4053* (2013.01); *A61B 1/00009* (2013.01); *A61B 1/0005* (2013.01); *G06T 3/4046* (2013.01); *H04N 23/85* (2023.01)

(58) Field of Classification Search
CPC . G06T 3/4053; G06T 3/4046; A61B 1/00009; A61B 1/0005; A61B 1/000095; A61B 1/000096; H04N 23/85; H04N 1/58; H04N 9/646; H04N 1/646; H04N 1/3935; H04N 9/67
See application file for complete search history.

(56) References Cited

U.S. PATENT DOCUMENTS

| | | | |
|---|---|---|---|
| 2020/0258197 A1* | 8/2020 | Tai | G06N 3/045 |
| 2021/0374911 A1* | 12/2021 | Kudo | G06N 3/047 |
| 2022/0182555 A1* | 6/2022 | Kawakami | A61B 1/00009 |
| 2022/0217260 A1* | 7/2022 | Kakidani | A61B 1/045 |
| 2023/0066267 A1* | 3/2023 | Kim | H04N 23/45 |
| 2023/0245442 A1* | 8/2023 | Narukiyo | G06V 10/764 382/224 |

FOREIGN PATENT DOCUMENTS

| | | |
|---|---|---|
| JP | 2020024612 | 2/2020 |
| WO | 2020175446 | 9/2020 |

* cited by examiner

*Primary Examiner* — Alazar Tilahun
(74) *Attorney, Agent, or Firm* — JCIPRNET

(57) ABSTRACT

An image processing apparatus acquires a color image including a plurality of primary color signals, performs color space conversion processing on the color image to generate a brightness signal image and a color difference signal image, performs super-resolution processing on the brightness signal image and the color difference signal image to generate a prediction brightness signal image, and uses the prediction brightness signal image to generate a super-resolution color image in which a resolution of the color image is increased.

17 Claims, 9 Drawing Sheets

IMAGE PROCESSING APPARATUS, IMAGE PROCESSING METHOD, NON-TRANSITORY COMPUTER READABLE MEDIUM, AND ENDOSCOPE SYSTEM

CROSS-REFERENCE TO RELATED APPLICATIONS

This application claims priority under 35 U.S.C § 119(a) to Japanese Patent Application No. 2022-134467 filed on 25 Aug. 2022. The above application is hereby expressly incorporated by reference, in its entirety, into the present application.

BACKGROUND OF THE INVENTION

1. Field of the Invention

The present invention relates to an image processing apparatus, an image processing method, a non-transitory computer readable medium, and an endoscope system.

2. Description of the Related Art

A super-resolution technique using deep learning makes it possible to generate a super-resolution image, which is an image having a higher resolution, by being estimated from an image having a low resolution. As a deep learning network for generating the super-resolution image, generative adversarial networks (GAN), a U-Net, or the like is used.

In addition, the super-resolution is also being considered to be performed on a medical image in the medical field. Development has been made to provide information supporting a diagnosis of a doctor by clarifying a CT image using the super-resolution image of the medical image, to provide information supporting the interpretation of an examination result by classifying a lesion, a cell, or the like.

For example, there is known a super-resolution image generation method of a trained model that has been trained by using generative adversarial networks including a generator and a discriminator and implementing a self-attention mechanism only in a discriminator network (WO2020/175446A, corresponding to US2021/374911A1). In addition, there is known a method of generating a trained model that has been trained by using a U-Net using training data including training image data and identifier that identifies classification of the training image data, and generating a super-resolution image based on first image data and a classification score which is a probability of the identifier (JP2020-024612A).

SUMMARY OF THE INVENTION

In the super-resolution image generated by the super-resolution technique, a color change, a color shift, an edge shift, or the like may occur. As a result, in the generated super-resolution image, a sense of resolution may be deteriorated.

The present invention is to provide an image processing apparatus, an image processing method, a non-transitory computer readable medium, and an endoscope system that generate a super-resolution image in which image qualities, such as a resolution and a sense of resolution, are improved.

An aspect of the present invention relates to an image processing apparatus comprising a processor, in which the processor acquires a color image including a plurality of primary color signals, performs color space conversion processing on the color image to generate a brightness signal image and a color difference signal image, performs super-resolution processing on the brightness signal image and the color difference signal image to generate a prediction brightness signal image, and uses the prediction brightness signal image to generate a super-resolution color image in which a resolution of the color image is increased.

It is preferable that the processor performs enlargement processing, which is different from the super-resolution processing, on the color difference signal image to generate an enlargement color difference signal image, and performs inverse conversion processing on the prediction brightness signal image and the enlargement color difference signal image to generate the super-resolution color image.

It is preferable that the enlargement processing is simple enlargement processing or upsampling processing.

It is preferable that the super-resolution processing is processing using a convolutional neural network.

It is preferable that the super-resolution processing includes upsampling processing or deconvolution processing.

It is preferable that the super-resolution processing is processing using a U-Net.

It is preferable that the processor includes a trained model, and performs the super-resolution processing by the trained model.

It is preferable that the processor includes a learning model, the learning model includes a plurality of parameters set in advance, the plurality of parameters are updated to generate the trained model, the plurality of parameters are updated by using a loss value, and the loss value is obtained by performing the color space conversion processing on a training image including the plurality of primary color signals to generate a color conversion image, performing deterioration processing on the color conversion image to generate a training brightness signal image, and then comparing a training prediction brightness signal image generated by performing the super-resolution processing based on the training brightness signal image with the training image.

It is preferable that the trained model includes a plurality of parameters, the plurality of parameters are updated by using a loss value, and the loss value is obtained by performing the color space conversion processing on a training image including the plurality of primary color signals to generate a color conversion image, performing deterioration processing on the color conversion image to generate a training brightness signal image, and then comparing a training prediction brightness signal image generated by performing the super-resolution processing based on the training brightness signal image with the training image.

It is preferable that the image processing apparatus further comprises two networks that are different from each other and perform the super-resolution processing to generate two training prediction brightness signal images different from each other, respectively, in which the processor uses the training prediction brightness signal images obtained by the two networks, respectively, to obtain two loss values, and uses the two loss values to update the plurality of parameters.

It is preferable that the processor performs the super-resolution processing once on a processed image including the brightness signal image and the color difference signal image.

It is preferable that an endoscope image captured by using an endoscope is acquired as the color image.

Another aspect of the present invention relates to an image processing method comprising a step of acquiring a color image including a plurality of primary color signals, a step of performing color space conversion processing on the color image to generate a brightness signal image and a color difference signal image, a step of performing super-resolution processing on the brightness signal image to generate a prediction brightness signal image, and a step of using the prediction brightness signal image to generate a super-resolution color image in which a resolution of the color image is increased.

Still another aspect of the present invention relates to a non-transitory computer readable medium for storing a computer-executable program for causing a computer to execute a function of acquiring a color image including a plurality of primary color signals, a function of performing color space conversion processing on the color image to generate a brightness signal image and a color difference signal image, a function of performing super-resolution processing on the brightness signal image to generate a prediction brightness signal image, and a function of using the prediction brightness signal image to generate a super-resolution color image in which a resolution of the color image is increased.

Still another aspect of the present invention relates to an endoscope system comprising an endoscope that images a subject to generate an endoscope image, a display that displays the endoscope image, and an image processing apparatus that includes a processor and generates a super-resolution endoscope image in which a resolution of the endoscope image is increased, in which the processor acquires the endoscope image as a color image, generates the super-resolution endoscope image in which the resolution of the endoscope image is increased, and performs control of displaying the super-resolution endoscope image on the display.

It is preferable that the processor displays the super-resolution endoscope image on the display, and displays an indicator indicating that a displayed image is the super-resolution endoscope image.

It is preferable that the image processing apparatus is the image processing apparatus described above.

According to the present invention, it is possible to generate the super-resolution image in which the resolution is improved.

DESCRIPTION OF THE PREFERRED EMBODIMENTS

Figure 1:
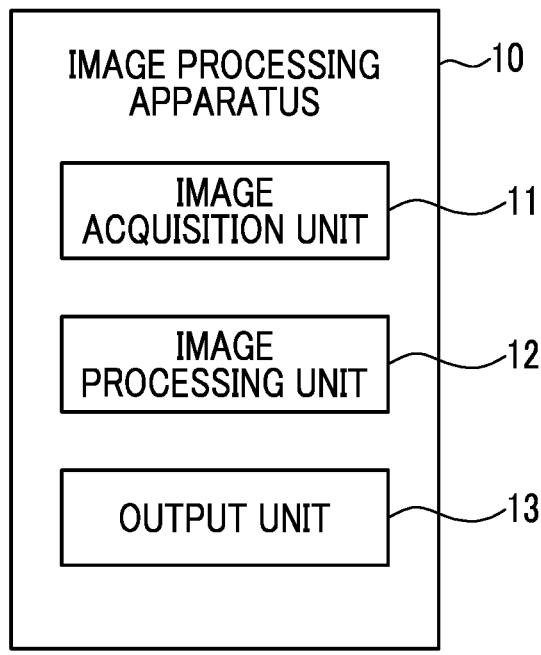
FIG. 1 is a block diagram showing a function of an image processing apparatus.

Hereinafter, an embodiment will be described with reference to the drawings as appropriate. First, a process leading to obtaining the following embodiment will be described. In recent years, deep learning using a neural network having a multi-layer structure enables highly accurate automatic image recognition as long as there is data on an image and its answer. In the field of segmentation, the downsampling and upsampling processing called a U-Net, a convolutional neural network (CNN) using a skip connection, and the like enable highly accurate segmentation. In addition, it is also possible to generate an image by a method called a GAN.

A super-resolution method of restoring a deterioration image that is deteriorated due to a decrease of a resolution or the like to the original state by using these methods is also studied. Restoring to the original state means that the deterioration image is restored to the image in a state in which the resolution is high before the resolution is decreased. It should be noted that, in the present specification, high resolution means that information on a high-frequency component is included in addition to the number of pixels in the image. Therefore, improving the resolution means that, in addition to an increase of the number of pixels, a sense of resolution is increased by adding the high-frequency component, reducing a color shift, a noise, and the like. On the other hand, the decrease of the resolution means that the sense of resolution is decreased due to the decrease of number of pixels in the image and/or the decrease of the information on the high-frequency component. The super-resolution means to improve the resolution, processing of performing the super-resolution is called super-resolution processing, and an image generated by performing the super-resolution processing is called a super-resolution image. Further, an image quality is a quality of an image including the resolution.

For example, by inputting the deterioration image to the CNN and comparing an image before the deterioration with the output of the CNN, the increase of the image quality in which the resolution is improved is learned. However, although an information amount can be increased by using an image including color information, there is a case in which a problem, such as the color shift, occurs in the increase of the resolution. The problem, such as the color shift, may cause the decrease of the resolution or the sense of resolution in the generated super-resolution image.

In the following embodiment, an image processing apparatus, an image processing method, an image processing program, and an endoscope system that generate a super-resolution image in which a resolution is improved will be described.

An example of a basic configuration of the image processing apparatus according to the embodiment of the present invention will be described. An image processing apparatus according to the embodiment of the present invention is a computer, such as a personal computer or a workstation, in which an application program for implementing a predetermined function is installed. The computer comprises a central processing unit (CPU) which is a processor, a memory, a storage, and the like, and various functions are implemented by a program stored in the storage and the like. In addition, the computer or the like may include a communication unit that enables communication with another computer or the like via a network or the like, a display unit, such as a display, an input unit, such as a touch panel or a keyboard, and the like.

As shown in FIG. 1, an image processing apparatus 10 comprises an image acquisition unit 11, an image processing unit 12, and an output unit 13 as functional configuration units. The image acquisition unit 11 has a function of acquiring a color image including a plurality of primary color signals. The image processing unit 12 has a function of performing processing on the color image acquired by the image acquisition unit 11 to generate a super-resolution color image. The output unit 13 has a function of outputting the super-resolution color image generated by the image processing unit 12 to a storage unit (not shown), a display, or the like. Each of these functional configuration units in the image processing apparatus 10 is implemented as the program that causes the computer to function.

The color image including the plurality of primary color signals acquired by the image acquisition unit 11 may be any color image as long as the color image includes the plurality of primary color signals, but is mainly an RGB image including the primary color signals of three colors of an R image consisting of a red signal value R, a G image consisting of a green signal value G, and a B image consisting of a blue signal value B. It should be noted that the primary color signal is not limited to these three colors, and may be other three colors, two colors, four colors, or the like. The image acquisition unit 11 acquires the RGB image of which the resolution is desired to be improved.

The image processing unit 12 performs processing of converting the RGB image acquired by the image acquisition unit 11 into the super-resolution color image in which the resolution is increased. The super-resolution color image is the RGB image consisting of the R image, the B image, and the G image.

Figure 2:
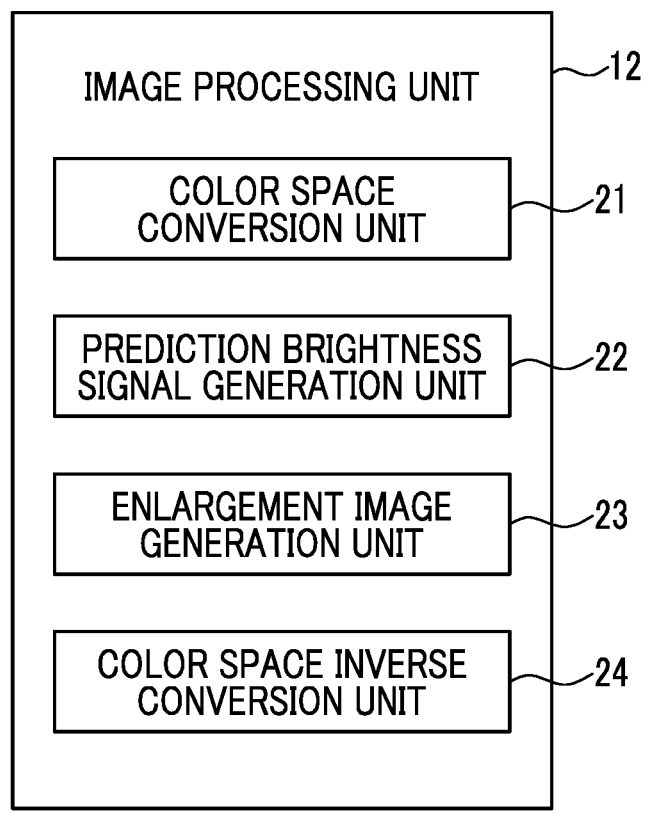
FIG. 2 is a block diagram showing a function of an image processing unit.

As shown in FIG. 2, the image processing unit 12 comprises a color space conversion unit 21, a prediction brightness signal generation unit 22, an enlargement image generation unit 23, and a color space inverse conversion unit 24 as functional configuration units. The color space conversion unit 21 has a function of performing color space conversion processing on the RGB image acquired by the image acquisition unit 11 to convert the RGB image into a YUV image. The YUV image includes a Y image that is an image with a brightness signal value Y, and a U image and a V image that are images with color difference signal values U and V. The prediction brightness signal generation unit 22 has a function of generating a prediction brightness signal image, which is the super-resolution image of the brightness signal image, by using the YUV image. The enlargement image generation unit 23 has a function of performing enlargement processing on the color difference signal image to generate an enlargement color difference signal image. The color space inverse conversion unit 24 has a function of converting the prediction brightness signal image and the enlargement color difference signal image into the RGB image.

Figure 3:
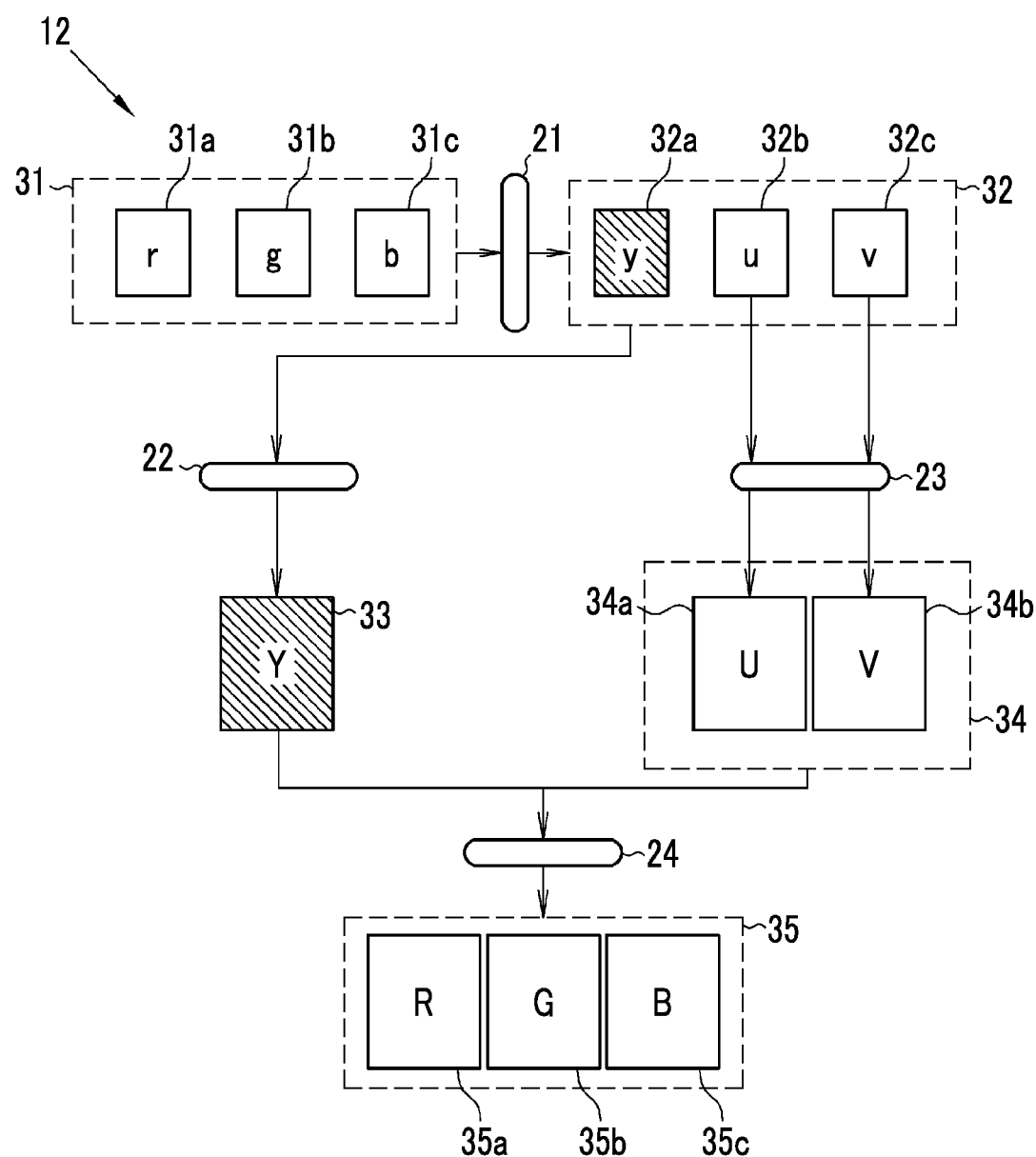
FIG. 3 is an explanatory diagram showing a flow of processing of the image processing unit.

As shown in FIG. 3, in a workflow by each functional configuration unit of the image processing unit 12, an input rgb image 31 acquired by the image acquisition unit 11 is subjected to the super-resolution processing and output as a super-resolution RGB image 35. The super-resolution RGB image 35 consists of a super-resolution R image 35a, a super-resolution G image 35b, and a super-resolution B image 35c. The image processing unit 12 acquires the input rgb image 31 acquired by the image acquisition unit 11. In the present embodiment, the input rgb image 31 includes an r image 31a, a g image 31b, and a b image 31c, each of which has the number of pixels of 512×512 pixels.

It should be noted that, in the present specification, a numerical value indicating the number of pixels of the image is in a unit of a pixel. In addition, the R image and the r image indicate images with the red signal values R and r, respectively, the G image and the g image indicate images with the green signal values G and g, respectively, and the B image and the b image indicate images with the blue signal values B and b, respectively. Further, the images indicated by the uppercase letters, such as the R image, the G image, and the B image, have a larger number of pixels than the images indicated by the lowercase letters, such as the r image, the g image, and the b image.

The color space conversion unit 21 performs the color space conversion processing on the input rgb image 31. The color space conversion processing is processing of converting the RGB image into the brightness signal image and the color difference signal image. It is known that the RGB image can be converted into the brightness signal image and the color difference signal image. Since the RGB image stores an image structure redundantly, in the field of image compression, the color space may be converted into the brightness signal and the color difference signal, and a representative example thereof is joint photographic experts group (JPEG). In the JPEG, in the process of encoding, the RGB image is converted into the brightness signal Y and color difference signals Cb and Cr, the downsampling of the color difference signals Cb and Cr, which are not considered to significantly affect the image quality, is performed with (4:2:2) as (Y:Cb:Cr), and the upsampling is performed by decoding.

As a method of the color space conversion processing, the color space conversion unit 21 can use various types of formats in addition to the format used for the JPEG. In the present embodiment, the RGB image is converted into the YUV image by the method used for a color composite video signal. In this method, the conversion from the RGB image to the YUV image can be performed by Expressions (1) to (3). In Expressions (1) to (3), R is the red signal value in the RGB image, G is the green signal value in the RGB image, B is the blue signal value in the RGB image, Y is the brightness signal value in the YUV image, U is the color difference signal value of U in the YUV image, and V is the color difference signal value of V in the YUV image. In addition, the brightness signal value Y, and the color difference signal values U and V are calculated for each pixel of the input rgb image 31. It should be noted that, as in a case of the RGB image, the Y image and the y image indicate images with the brightness signal values Y and y, respectively, the U image and the u image indicate images with the color difference signal values U and u, respectively, the V image and the v image indicate images with the color difference signal values V and v, respectively, and the images indicated by the uppercase letters, such as the Y image, the U image, and the V image, have a larger number of pixels than the images indicated by the lowercase letters, such as the y image, the u image, and the v image.

$$Y=(0.29900*R)+(0.58700*G)+(0.11400*B) \quad (1)$$

$$U=(-0.14713*R)+(-0.28886*G)+(0.43600*B) \quad (2)$$

$$V=(0.61500*R)+(-0.51499*G)+(-0.10001*B) \quad (3)$$

In the present embodiment, since the input rgb image 31 is an rgb image including the r image 31a, the g image 31b, and the b image 31c, the brightness signal image and the color difference signal image obtained by performing the color space conversion processing on the input rgb image 31 are input yuv images 32 including a y image 32a, a u image 32b, and a v image 32c, each of which has 512×512 pixels. The prediction brightness signal generation unit 22 receives the input yuv image 32 and performs processing on the input yuv image 32.

The prediction brightness signal generation unit 22 performs the super-resolution processing on the brightness signal image and the color difference signal image to generate the prediction brightness signal image. Since the prediction brightness signal image is an image obtained by performing the super-resolution processing on the brightness signal image or the like, the prediction brightness signal image has a higher resolution than the brightness signal image. In the present embodiment, the brightness signal image and the color difference signal image are the input yuv images 32 including the y image 32a, which is the brightness signal image, and the u image 32b and the v image 32c, which are the color difference signal images, and the prediction brightness signal image 33 is the Y image 33a having a higher resolution than the y image 32a. Both the y image 32a and the Y image 33a are images of the brightness signals.

Figure 4:
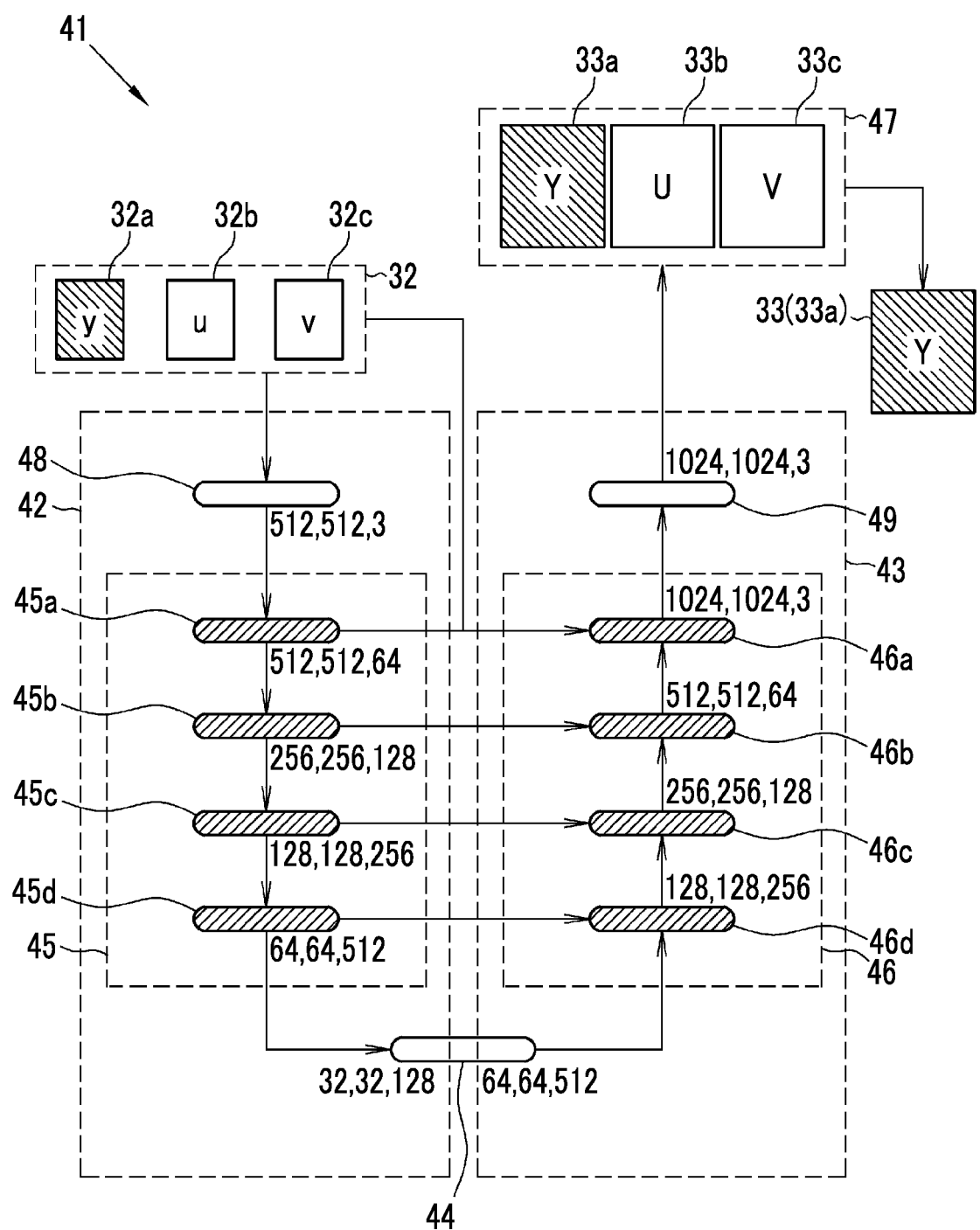
FIG. 4 is an explanatory diagram showing a flow of processing of a prediction brightness signal generation model.

The prediction brightness signal generation unit 22 generates the prediction brightness signal image 33 by using a prediction brightness signal generation model 41 (see FIG. 4). The prediction brightness signal generation model 41 can be used with any model as long as the model performs the super-resolution. However, it is preferable to use a model that performs the super-resolution by using the CNN in terms of a good prediction brightness signal image 33 to be generated, and it is more preferable to use a model that performs the super-resolution by using the U-Net in terms of a good prediction brightness signal image 33 to be generated.

It should be noted that, in the present specification, the "model" refers to the series of algorithms for processing the input, and includes a model that has not been trained for adjustment of the parameters and the like, a model of which at least a part has been trained, and a model in which a model has been trained to be a trained model once, and then the trained model has been trained again to update the parameters and the like. In the "model", the "trained model" particularly refers to a model in which training is performed on at least a part of the model using training data or the like. Therefore, a model generated by training the trained model again is also included in the "trained model". The prediction brightness signal generation model 41 is the trained model. The generation of the prediction brightness signal generation model 41 by training will be described below.

The U-Net is a model consisting of a fully convolution network (FCN) using the CNN, and is used for semantic segmentation, but it is known that an architecture of the U-Net is also used for implementing the super-resolution (see "Image Restoration Using Very Deep Convolutional Encoder-Decoder Networks with Symmetric Skip Connections" CVPR2016, (United States of America), 4/2016, p. 210).

In the prediction brightness signal generation model 41 (see FIG. 4), the architecture of the U-Net comprising an encoder, a folded layer, and a decoder is adopted. The encoder and the decoder each comprise an intermediate layer consisting of one or two or more hierarchies. The folded layer is connected to the intermediate layer on the most downstream side of the encoder and the intermediate layer on the most upstream side of the decoder.

In the intermediate layer of the encoder, the input image is subjected to processing of generating a feature map by performing convolution processing using a plurality of kernels, or generating a feature map by performing convolution processing using a plurality of kernels after performing the downsampling of decreasing the number of pixels as compared with the feature map input to the intermediate layer by pooling processing. Therefore, it can be said that the processing in the encoder is processing using the CNN. Further, the pooling processing is one type of the downsampling. The feature map is a feature amount indicating a feature of the input image, which is extracted by each kernel in convolution processing, and is a tensor consisting of vertical and horizontal sizes of a convolution result, the number of channels, and the like. In the feature map, the vertical size, the horizontal size, and the number of channels are collectively referred to as the number of elements. The channel means data of a component, such as a color in each pixel of the image or the convolution result, and the number of channels indicates the number of data in each pixel of the image or the convolution result. It should be noted that, in the convolution result, the size is the same as the number of pixels. The convolution result or the tensor is one type of image data.

The folded layer has the functions of the encoder and the decoder, performs the convolution processing using the plurality of kernels after performing the downsampling by the pooling processing of decreasing the vertical and horizontal sizes of the convolution result included in the feature map input to the folded layer, and then performs the upsampling of increasing the vertical and horizontal sizes of the convolution result included in the feature map by the deconvolution processing. It should be noted that information amount decrease processing may be performed on the feature amount map in the folded layer. The information amount decrease processing is processing of decreasing the information amount, and it is possible to adopt conversion of a data type, decrease of the number of elements of the feature map, and the like. Therefore, the information amount can be represented by the number of elements, the number of bits, and the like of the feature map. As described below, the number of elements of the feature map can be represented as a combination of the vertical size, the horizontal size, and the number of channels of the image, the convolution result, and the like. The number of bits can be obtained from the number of elements and the data type.

In the intermediate layer of the decoder, the vertical and horizontal sizes of the convolution result included in the feature map are increased by the upsampling with respect to the feature map. As a method of the upsampling, a method used as the upsampling processing on the image can be adopted, and examples thereof include a bilinear method, a bicubic method, an average pixel method, and deconvolution processing. As a method of the upsampling, it is preferable to adopt the deconvolution processing because good results can be obtained. It should be noted that the deconvolution processing can be processing in which the enlargement processing and the convolution processing on the convolution result included in the feature map to be processed are combined. Since inverse processing of the convolution processing and the pooling processing is performed in the processing in the decoder, it can be said that the processing is the processing using the CNN. In addition, it is preferable that the upsampling performed on the feature map in the intermediate layer of the decoder is processing having different contents from the upsampling performed in the enlargement processing performed on the color difference signal image described below.

In each intermediate layer of the encoder, in addition to performing the convolution processing and the like, the feature map generated in each intermediate layer of the encoder is passed to the intermediate layer of the decoder of the hierarchy corresponding to each intermediate layer of the encoder. In the U-Net, since the decoder can use the feature map output from the intermediate layer of the encoder, it is possible to implement the super-resolution with extremely high accuracy. Therefore, it is preferable to set the number of intermediate layers of each hierarchy in the decoder such that the feature map can be received from the intermediate layer of each hierarchy of the encoder, and it is more preferable to set the number of intermediate layers to the same number in each of the encoder and the decoder. In addition, in order to prevent a large difference in the number of pixels between the feature map received by the intermediate layer of the decoder from the intermediate layer of the encoder and the feature map received by the intermediate layer of the decoder from the intermediate layer of the upstream hierarchy, it is preferable that the number of pixels to be increased or decreased by the downsampling or the upsampling is approximately the same in the respective intermediate layers of the corresponding hierarchies in the encoder and the decoder although the number of pixels depends on the presence or absence of padding or the like. In addition, in the feature map passed from the intermediate layer of the encoder, a part, such as a central portion, of the feature map from the encoder may be selected as the feature map, and then the feature map may be received by the intermediate layer of the decoder. It should be noted that the number of hierarchies of the intermediate layers in the encoder and the decoder is appropriately determined depending on the case.

An adjustable item in the processing performed on the encoder, the decoder, and the folded layer can be appropriately set. Examples of the adjustable item include the number of times of the convolution processing, the size of the kernel, the number of channels, the method of the downsampling or the upsampling, and the size decreased by the pooling processing or the size increased by the deconvolution processing. It should be noted that the training may include adjustment of these adjustable items in addition to update of the parameters of the model.

In the present embodiment, the prediction brightness signal generation model 41 is the trained model that has been trained using the U-Net, has been trained to preferably output the Y image 33a, which is the super-resolution image of the y image 32a, in response to the input of the input yuv image 32, and is subjected to various adjustments of items such as the parameters. In the prediction brightness signal generation model 41 (see FIG. 4), the super-resolution image in which the number of pixels is increased as compared with the input yuv image 32 is generated and output by the encoder and the decoder.

As shown in FIG. 4, the prediction brightness signal generation model 41 according to the present embodiment is a network consisting of the architecture of the U-Net comprising an encoder 42 and a decoder 43. In the present embodiment, the encoder 42 comprises an intermediate layer 45 consisting of an intermediate layer 45a, an intermediate layer 45b, an intermediate layer 45c, and an intermediate layer 45d, and a folded layer 44. The decoder 43 comprises an intermediate layer 46 consisting of an intermediate layer 46a, an intermediate layer 46b, an intermediate layer 46c, and an intermediate layer 46d. In FIG. 4, the intermediate layer is added with diagonal lines. In addition, the numerical character described below or above along with the figure showing each layer indicates the number of elements of the feature map or the image consisting of the convolution result output by each layer, and the vertical size, the horizontal size, and the number of channels of the image or the like are indicated by the numerical characters in this order. In a case in which each intermediate layer of the encoder 42 or the decoder 43 is not distinguished, the intermediate layer is referred to as the intermediate layer 45 or the intermediate layer 46.

The prediction brightness signal generation model 41 may include an input layer 48 and an output layer 49 that perform processing or the like for subsequent processing. The input layer 48 and the output layer 49 perform the conversion of the data type and the like. The input yuv image 32 is first input to the input layer 48 and then input to the first intermediate layer 45a of the encoder 42. Further, the feature map output from the last intermediate layer 46a of the decoder 43 is input to the output layer 49, and processing of obtaining a super-resolution YUV image 47 consisting of the Y image 33a, the U image 33b, and the V image 33c is performed in the output layer 49.

The input yuv image 32 input to the input layer 48 is passed to the intermediate layer 46a after changing the data type of the input yuv image 32. In the input yuv image 32 and the yuv image output by the input layer 48, the vertical size, the horizontal size, and the number of channels of the image are 512, 512, and 3, respectively.

In the first intermediate layer 45a of the encoder 42, the feature map having the plurality of channels is generated by performing the convolution processing using the plurality of kernels on the input yuv image 32. In the feature map output by the intermediate layer 45a, the number of elements of the convolution result is 512, 512, and 64, respectively. The intermediate layer 45a passes the generated feature map to the intermediate layer 45b of the downstream hierarchy of the encoder 42 and the corresponding intermediate layer 46a of the decoder 43.

In the intermediate layer 45b of the downstream hierarchy of the encoder 42, the number of pixels of the feature map is decreased by performing the pooling processing on the feature map passed from the intermediate layer 45a of the upstream hierarchy. Thereafter, the feature map having the plurality of channels is generated by performing the convolution processing using the plurality of kernels. In the feature map output by the intermediate layer 45b, the number of elements of the convolution result is 256, 256, and 128, respectively. The intermediate layer 45b passes the generated feature map to the intermediate layer 45c of the downstream hierarchy of the encoder 42 and the corresponding intermediate layer 46b of the decoder 43.

Hereinafter, the same processing is repeated for each intermediate layer 45 of the encoder 42. That is, in the intermediate layer 45c on the immediately downstream side of the intermediate layer 45b, the number of pixels of the feature map is decreased by performing the pooling processing on the feature map passed from the intermediate layer 45b of the upstream hierarchy. Thereafter, the feature map having the plurality of channels is generated by performing the convolution processing using the plurality of kernels. The intermediate layer 45c passes the generated feature map to the intermediate layer 45d of the downstream hierarchy of the encoder 42 and the corresponding intermediate layer 46c of the decoder 43.

In the pooling processing in the intermediate layer 45 of the encoder 42, processing of decreasing the number of pixels by half is performed. In addition, the feature map having 64 channels is generated in the convolution processing in the first intermediate layer 45a, and the feature map in which the number of channels is twice the number of channels in the immediately preceding intermediate layer 45 is generated in the convolution processing in each intermediate layer 45 other than the intermediate layer 45a. In this way, in the intermediate layer 45d on the most downstream side of the encoder 42, the feature map in which the number of elements of the convolution result is 64, 64, and 512 and the number of pixels or the information amount is decreased is generated based on the input yuv image 32. The feature map generated by the intermediate layer 45d on the most downstream side of the encoder 42 is passed to the folded layer 44.

In the folded layer 44, both the downsampling processing and the upsampling processing are performed in this order. Therefore, in FIG. 4, the folded layer 44 is shown as including both the encoder 42 that performs the downsampling processing and the decoder 43 that performs the upsampling processing.

In the folded layer 44, the number of pixels of the feature map is decreased by performing the pooling processing on the feature map received from the intermediate layer 45d. Thereafter, the feature map having the plurality of channels is generated by performing the convolution processing using the plurality of kernels. In the feature map in this case, the number of elements of the convolution result is 32, 32, and 1024.

Here, in the folded layer 44, information amount decrease processing may be performed to decrease the number of channels of the feature map. In the present embodiment, the feature map in which the number of elements of the convolution result is 32, 32, and 1024 is converted into the feature map in which the number of elements of the convolution result is 32, 32, and 128 by the information amount decrease processing.

Next, in the folded layer 44, the feature map having the plurality of channels is generated by performing the deconvolution processing using the plurality of kernels. As a result, in the feature map output by the folded layer 44, the number of elements of the convolution result is 64, 64, and 512. The feature map generated by the folded layer 44 is output to the intermediate layer 46d on the most upstream side of the decoder 43.

In the intermediate layer 46d on the most upstream side of the decoder 43, the feature map having the plurality of channels is generated by performing the deconvolution processing using the plurality of kernels on a combination of the feature map passed from the folded layer 44 and the feature map passed from the corresponding intermediate layer 45d of the encoder 42. In the feature map output by the intermediate layer 46d, the number of elements of the convolution result is 128, 128, and 256. The intermediate layer 46d passes the generated feature map to the intermediate layer 46c of the decoder 43 of the next downstream hierarchy.

Next, in the intermediate layer 46c on the downstream side, the received feature map is subjected to the same processing as the processing performed in the intermediate layer 46d on the upstream side. That is, in the intermediate layer 46c of the decoder 43, the feature map having the plurality of channels is generated by performing the deconvolution processing using the plurality of kernels on a combination of the feature map passed from the intermediate layer 46d of the upstream hierarchy and the feature map passed from the corresponding intermediate layer 45c of the encoder 42. In the feature map output by the intermediate layer 46c, the number of elements of the convolution result is 256, 256, and 128. The intermediate layer 46c passes the generated feature map to the intermediate layer 46b of the decoder 43 of the next downstream hierarchy. In a case in which the intermediate layer 46 consists of a plurality of hierarchies, these pieces of processing are repeated in the intermediate layer 46 of each hierarchy.

Hereinafter, the same processing is repeated for each intermediate layer 46 in the decoder 43. That is, in the intermediate layer 46b on the next downstream side of the intermediate layer 46c, the feature map having the plurality of channels is generated by performing the deconvolution processing using the plurality of kernels on a combination of the feature map passed from the intermediate layer 46c of the upstream hierarchy and the feature map passed from the corresponding intermediate layer 45b of the encoder 42. The intermediate layer 46b passes the generated feature map to the intermediate layer 46a of the decoder 43 of the next downstream hierarchy.

It should be noted that, in the intermediate layer 46a on the most downstream side of the decoder 43, the processing may be performed on a combination of the feature map passed from the intermediate layer 46b of the upstream hierarchy, the feature map passed from the corresponding intermediate layer 45a of the encoder 42, and further the input yuv image 32. The intermediate layer 46a generates the feature map having the plurality of channels by performing the deconvolution processing using the plurality of kernels on the combination of the three described above. In the feature map output by the intermediate layer 46a, the number of elements of the convolution result is 1024, 1024, and 32. The feature map output by the intermediate layer 46a is input to the output layer 49.

The output layer 49 receives the feature map output by the intermediate layer 46a on the most downstream side of the decoder 43. The output layer 49 adjusts the number of channels, converts the data type, and outputs the super-resolution YUV image 47 in which the number of elements of the image is 1024, 1024, and 3. The super-resolution YUV image 47 includes the Y image 33a, the U image 33b, and the V image 33c, and the three channels correspond to three of one brightness signal image and two color difference signal images.

As described above, since the prediction brightness signal generation model 41 is a model designed and trained to preferably output the Y image 33a, which is the super-resolution image of the y image 32a, the prediction brightness signal generation model 41 can preferably output the Y image 33a, which is the super-resolution image of the y image 32a, in response to the input of the input yuv image 32. The Y image 33a is the prediction brightness signal image 33.

The enlargement image generation unit 23 generates the enlargement color difference signal image by performing the enlargement processing on the color difference signal image. The enlargement processing performed by the enlargement image generation unit 23 is processing different from the super-resolution processing. As shown in FIG. 3, in the present embodiment, the enlargement image generation unit 23 performs the enlargement processing on the u image and the v image included in the input yuv image 32 to generate an enlargement color difference signal image 34 consisting of the U image and the V image in which the number of pixels is increased as compared with the u image and the v image included in the input yuv image 32.

The enlargement processing performed by the enlargement image generation unit 23 need only be any processing different from the super-resolution processing performed for generating the prediction brightness signal image 33, and includes the simple enlargement processing, the upsampling processing, and the like. The simple enlargement processing is processing of simply enlarging the vertical and horizontal sizes of each pixel to increase the number of pixels. The upsampling processing is processing of increasing the number of pixels while complementing the pixel values of the increased pixels by calculation. In the upsampling processing, various methods can be adopted. Examples of the upsampling processing in the image include the bilinear method, the bicubic method, and the average pixel method.

The number of pixels of the enlargement color difference signal image 34 generated by the enlargement processing performed by the enlargement image generation unit 23 is the same as the number of pixels of the prediction brightness signal image 33. Therefore, in the present embodiment, since the u image 32b and the v image 32c each have 512×512 pixels, the vertical and horizontal sizes of each of these images are enlarged twice, and the U image 34a and the V image 34b have 1024×1024 pixels, which are the same as the pixels of the y image 32a which is the prediction brightness signal image 33.

The color space inverse conversion unit 24 performs color space inverse conversion on the prediction brightness signal image 33 and the enlargement color difference signal image 34 to generate the super-resolution RGB image 35. In the present embodiment, the conversion expressions according to Expressions (4) to (6) are used according to the method used for the color composite video signal, as in a case of the conversion of the RGB image into the YUV image. In Expressions (4) to (6), R is the red signal value in the RGB image, G is the green signal value in the RGB image, B is the blue signal value in the RGB image, Y is the brightness signal value in the YUV image, U is the color difference signal value of U in the YUV image, and V is the color difference signal value of V in the YUV image. According to Expressions, the red signal value R, the green signal value G, and the blue signal value B, and the brightness signal value Y, the color difference signal value U, and the color difference signal value V can be converted into each other.

$$R=(1.00000*Y)+(0.00000*U)+(0.13983*V) \quad (4)$$

$$G=(1.00000*Y)+(-0.39465*U)+(-0.58060*V) \quad (5)$$

$$B=(1.00000*Y)+(2.03211*U)+(0.00000*V) \quad (6)$$

The output unit 13 outputs the super-resolution RGB image 35, which is the super-resolution image generated by the image processing apparatus 10, to the display unit, such as the display, the storage, or the like. In this case, the image processing apparatus 10 is connected to the display, the storage, or the like. It should be noted that, in a case in which the super-resolution RGB image 35 is output for display on the display, it is preferable to display the super-resolution RGB image 35 after showing, on the display, an indicator indicating that the image displayed on the display is not an image directly obtained by imaging the subject, but includes image data predicted by the super-resolution processing. Since the super-resolution RGB image 35 is not the image obtained by imaging the subject, but includes the image data predicted by the prediction brightness signal image 33 or the like, it is possible to prevent misunderstandings given to a doctor or the like during diagnosis or the like.

As described above, the image processing unit 12 can generate the super-resolution image in which the resolution is improved as compared with the input image. This super-resolution image can be the super-resolution image having an excellent resolution in which the color shift, the noise, and the like are suppressed. Normally, in a case in which the super-resolution is performed by the CNN, the RGB image is input and the RGB image is output. In this case, in the inference, the R image, the G image, and the B image should be inferred respectively, which may cause the color shift. In the image processing unit 12, the super-resolution image is generated by converting the RGB image into the brightness signal image and the color difference signal image, inputting the brightness signal image and the color difference signal image to the CNN, and outputting only the prediction brightness signal image 33, which is the Y image 33a, and the color difference signal image generates the super-resolution RGB image 35 by, for example, the simple enlargement processing. With the configuration described above, the super-resolution RGB image 35 is the super-resolution image having an excellent resolution in which the color shift, the noise, and the like are suppressed.

In addition, in the image processing unit 12, since the folded layer 44 of the prediction brightness signal generation model 41 is a model trained based on the model subjected to the information amount decrease processing, the generated prediction brightness signal image 33 can be an image having a high resolution to which a large amount of the high-frequency components is added as compared with the brightness signal image of the original image having a high resolution before the input rgb image 31 used for the training is deteriorated. Therefore, with the configuration as described above, even in a case in which the number of pixels is the same, the super-resolution RGB image 35 generated by the image processing apparatus 10 including the image processing unit 12 can be an image having a high image quality than the original image having a high resolution before the deterioration by suppressing the color shift, the noise, and the like and adding a large amount of the high-frequency components.

Figure 5:
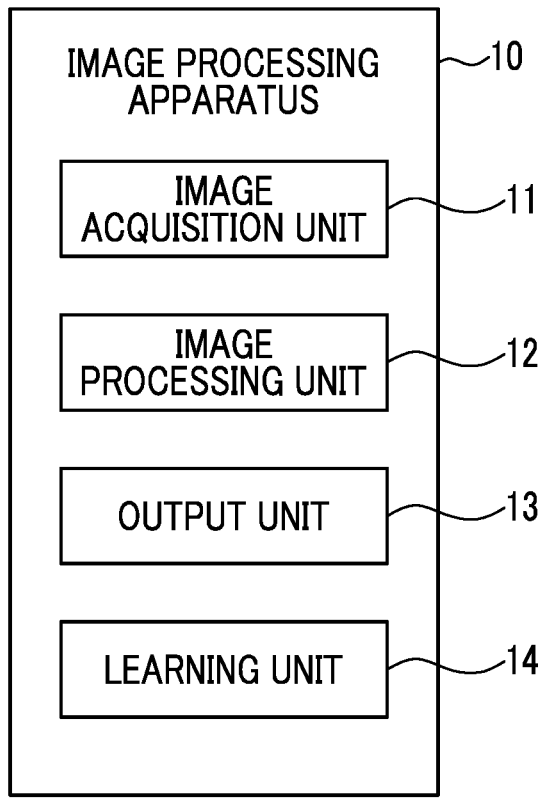
FIG. 5 is a block diagram showing a function of the image processing apparatus including a learning unit.

Next, the generation of the prediction brightness signal generation model 41 (see FIG. 4) will be described. The prediction brightness signal generation model 41 is a trained model that is generated by training a prediction brightness signal generation learning model (hereinafter, referred to as a learning model). As shown in FIG. 5, in a case of performing training for generating the prediction brightness signal generation model 41, the image processing apparatus 10 comprises a learning unit 14 as a functional configuration unit. The image processing unit 12 uses the prediction brightness signal generation model 41 generated by the learning unit 14.

The learning model before training includes a network consisting of the series of algorithms including a plurality of parameters set in advance. The trained model is generated by performing training that adjusts these parameters and the like. It should be noted that the training of the learning model may include adjustment of other adjustable items in the learning model in addition to adjustment of the parameters and the like included in the learning model.

Figure 6:
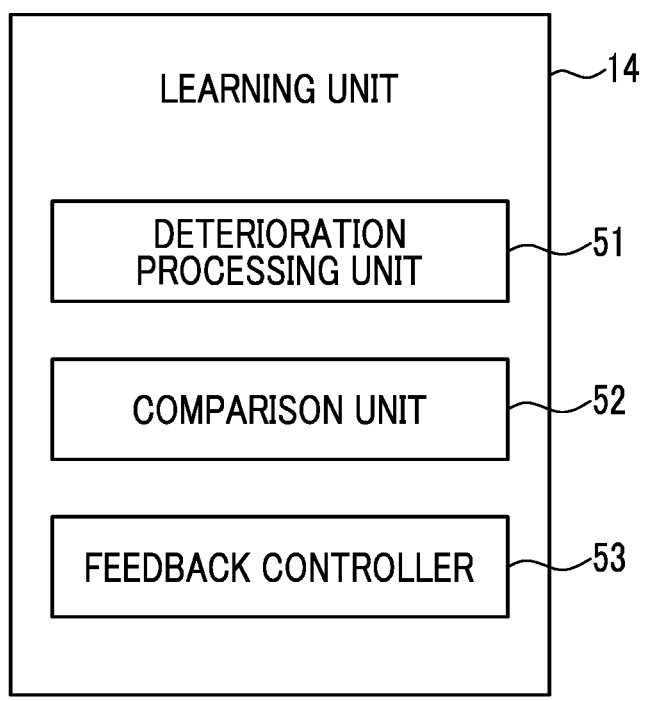
FIG. 6 is a block diagram showing a function of the learning unit.

As shown in FIG. 6, the learning unit 14 comprises, as functional configuration units, a deterioration processing unit 51 having a function of performing the deterioration processing on a source image, which is the training image including the plurality of primary color signals, a comparison unit 52 having a function of calculating a loss by comparing the image processed by the learning model with the source image, which is the training image, and a feedback controller 53 having a function of performing control of updating the parameters in the learning model by performing feeding back the loss calculated by the comparison unit 52 to the learning model. Since the source image is usually the RGB image, the target of the deterioration processing performed by the deterioration processing unit 51 is the source image converted into the YUV image which is a color conversion image by performing the color space conversion processing on the RGB image. The deterioration processing unit 51 performs the deterioration processing, such as decreasing the number of pixels on the source image, which is the YUV image, to generate the yuv image having a decreased resolution.

The learning model need only be a model that can perform processing of outputting the super-resolution image of the input image in a case in which the image is input to the prediction brightness signal generation model 41 generated by the training. Examples of the learning model that generates the super-resolution image include the GAN and the U-Net. In the present embodiment, a learning model in which a basic U-Net is partially changed is used. The basic U-Net is a network that includes an encoder and a decoder each consisting of one network, in which intermediate layers of the encoder and the decoder are connected to each other.

Figure 7:
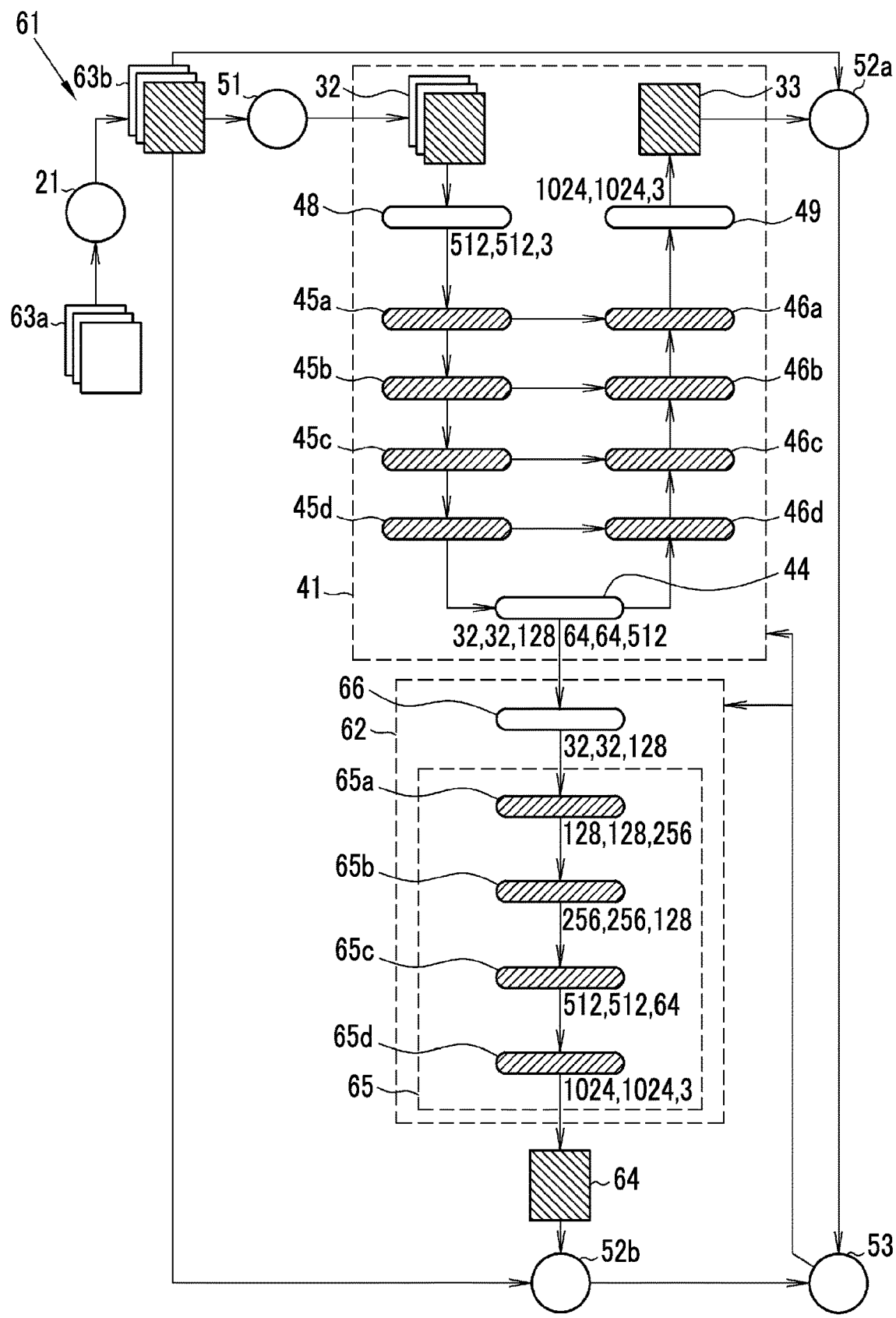
FIG. 7 is an explanatory diagram showing training of a learning model.

As shown in FIG. 7, a learning model 61 according to the present embodiment is a learning model partially modified by mainly adding configurations of two points in the U-Net including the encoder 42 and the decoder 43 having the same architecture as the prediction brightness signal generation model 41.

The first point is a point that a branched and independent branch network 62 is connected to the folded layer 44. The branch network 62 performs the upsampling separately from the decoder 43 to generate a sub-prediction brightness signal image 64. It should be noted that the branch network 62 is independent without being connected to other networks, such as the encoder 42. Therefore, since the processing is different from the processing in the decoder 43, the feature map unique to the branch network 62 can be generated.

The second point is a point that a comparison unit 52a and a comparison unit 52b that execute a function of calculating two types of losses by comparing a source image 63b of the YUV image which is teacher data with each of the prediction brightness signal image 33 and the sub-prediction brightness signal image 64 generated by the learning model, and the feedback controller 53 that executes a function of changing the parameters of the learning model such that the loss is minimized are provided. The prediction brightness signal image 33 and the sub-prediction brightness signal image 64 generated by the prediction brightness signal generation model 41 and the branch network 62 provided in the learning model 61, respectively, are training brightness signal images. It should be noted that, in a case in which the comparison unit 52a and the comparison unit 52b are not distinguished, the comparison unit 52a and the comparison unit 52b are referred to as the comparison unit 52.

For the training of the learning model 61, a source image 63a of the RGB image having a high resolution which is the teacher data is used. In order to compare with the prediction brightness signal image 33, which is the super-resolution image generated by the prediction brightness signal generation model 41, or the sub-prediction brightness signal image 64, which is the super-resolution image generated by the branch network 62, it is preferable to use an image in which a part of the image having a high resolution is cut out for the source image 63a or the source image 63b. The source image 63a is the color image including the plurality of primary color signals, and in the present embodiment, is the RGB image including the R image, the G image, and the B image. It should be noted that, in a case in which the source image 63a, which is the RGB image, and the source image 63b, which is the YUV image, are not distinguished in the source image, the source image 63a and the source image 63b are referred to as the source image 63.

It should be noted that, in FIG. 7, the source image 63a is the RGB image including the R image, the G image, and the B image. The source image 63b is the YUV image including the Y image, the U image, and the V image, and the input yuv image 32 is an image including one brightness signal and two color difference signals. The source image 63 and the input yuv image are each indicated by three rectangular figures. One rectangle indicates an image consisting of one image signal, and the shaded rectangle indicates an image consisting of the brightness signal. A circular figure indicates the processing unit, and a rectangular figure with rounded corners indicates each layer that is the processing unit of the learning model. It should be noted that, in the drawing, the same reference numeral indicates the same component.

The source image 63a, which is the RGB image, is first input to the color space conversion unit 21 and is subjected to the color space conversion processing to be the source image 63b, which is the YUV image. Thereafter, the deterioration processing is performed by the deterioration processing unit 51. Out of the deterioration processing and the color space conversion processing, the color space conversion processing is performed first, and then the deterioration processing is performed. As a result, the brightness signal having a high resolution included in the source image 63b can be used as the source image which is the training image. In the present embodiment, the source image 63 has the number of pixels of 1024×1024 pixels.

The color space conversion processing performed by the color space conversion unit 21 is the same as the color space conversion processing described in the prediction brightness signal generation model 41. The source image 63b, which is the YUV image, generated by the color space conversion processing is passed to the deterioration processing unit 51. The deterioration processing unit 51 performs the deterioration processing on the source image 63b, which is the YUV image, to generate the input yuv image 32, which is the deterioration image.

The deterioration processing means processing, such as decreasing the number of pixels in the image and/or decreasing the sense of resolution by decreasing the information of the high-frequency component. In the present embodiment, the source image 63b, which is the YUV image, is converted into the input yuv image 32, which is the deterioration image in which the number of pixels is decreased. The y image 32a (see FIG. 4) in the yuv image is the training brightness signal image. In the present embodiment, the input yuv image 32 has the number of pixels of 512×512 pixels.

As the deterioration processing, filter processing of applying a filter, noise addition processing of applying the noise, and the like may be performed. The deterioration processing may be performed with one type or a combination of two or more types of these pieces of processing. Since the performance of the super-resolution processing in the prediction brightness signal generation model 41, which is the trained model, may be affected by the deterioration processing, it is preferable to determine the content of the deterioration processing according to the target super-resolution processing.

As described in the prediction brightness signal generation model 41, the input yuv image 32 is input to the input layer 48 of the decoder 43, and then is input to the folded layer 44 through the processing by the intermediate layers 45a, 45b, 45c, and 45d of the decoder 43.

As described above, the folded layer 44 in the learning model 61 is connected to the branched and independent branch network 62. After performing the processing on the received feature map, the folded layer 44 outputs the feature map to the intermediate layer 46d on the most upstream side of the decoder 43, and outputs the feature map to the input layer 66 of the branch network 62.

The processing of the folded layer 44 is the same as the processing of the prediction brightness signal generation model 41 (see FIG. 4), and both the downsampling processing and the upsampling processing are performed in this order. In the folded layer 44, the number of pixels of the feature map is decreased by performing the pooling processing on the feature map received from the intermediate layer 45d. Thereafter, the feature map having the plurality of channels is generated by performing the convolution processing using the plurality of kernels. In this case, the feature map has the number of elements of 32, 32, and 1024.

Here, in the folded layer 44, the information amount decrease processing is performed to decrease the number of channels of the feature map. In the present embodiment, the feature map in which the number of elements of the convolution result is 32, 32, and 1024 is converted into the feature map in which the number of elements of the convolution result is 32, 32, and 128 by the information amount decrease processing.

Then, the feature map having the number of elements of 32, 32, and 128 is passed to the input layer 66 of the branch network and the next processing in the folded layer 44. In the next processing in the folded layer 44, the feature map having the plurality of channels is generated by performing the deconvolution processing using the plurality of kernels. As a result, in the feature map output by the folded layer 44, the number of elements of the convolution result is 64, 64, and 512. The feature map generated by the folded layer 44 is output to the intermediate layer 46d on the most upstream side of the decoder 43. The feature map output to the intermediate layer 46d on the most upstream side of the decoder 43 is subjected to the same processing that the feature map is passed through each intermediate layer of the decoder 43 in the prediction brightness signal generation model 41 (see FIG. 4), and the prediction brightness signal image 33, which is the Y image, is generated.

In the branch network 62, the feature map in which the number of elements received from the folded layer 44 by the input layer 66 is 32, 32, and 128 is passed from the input layer 66 to the intermediate layer 65 of the branch network 62. In the processing in the intermediate layer 65, the feature map having the plurality of channels is generated by performing the deconvolution processing using the plurality of kernels in the same manner as the processing in the intermediate layer 46 of the decoder 43 (see FIG. 4). It should be noted that, unlike the intermediate layer 46, in the processing in the intermediate layer 65 of the branch network 62, the information is not input from other sources including the intermediate layer 45 of the encoder 42, and the processing is performed by the branch network 62 alone.

In the present embodiment, the intermediate layer 65 has four hierarchies of an intermediate layer 65a, an intermediate layer 65b, an intermediate layer 65c, and an intermediate layer 65d. In the intermediate layer 65a on the most upstream side of the branch network 62, the feature map having the plurality of channels is generated by performing the deconvolution processing using the plurality of kernels on the feature map passed from the folded layer 44. In the feature map output by the intermediate layer 65a, the number of elements of the convolution result is 128, 128, and 256. The intermediate layer 65a passes the generated feature map to the intermediate layer 65b of the next downstream hierarchy of the branch network 62.

Next, in the intermediate layer 65b on the downstream side, the received feature map is subjected to the same processing as the processing performed in the intermediate layer 65a on the upstream side. That is, in the intermediate layer 65b of the branch network 62, the feature map having the plurality of channels is generated by performing the deconvolution processing using the plurality of kernels on the feature map passed from the intermediate layer 65a of the upstream hierarchy. In the feature map output by the intermediate layer 65b, the number of elements of the convolution result is 256, 256, and 128. The intermediate layer 65b passes the generated feature map to the intermediate layer 65c of the next downstream hierarchy of the branch network 62. In a case in which the intermediate layer 65 consists of a plurality of hierarchies, these pieces of processing are repeated in the intermediate layer 65 of each hierarchy.

Hereinafter, the same processing is repeated in each intermediate layer 65 in the branch network 62. That is, in the intermediate layer 65c on the next downstream side of the intermediate layer 65b, the feature map having the plurality of channels is generated by performing the deconvolution processing using the plurality of kernels on the feature map passed from the intermediate layer 65b of the upstream hierarchy. The intermediate layer 65c passes the generated feature map to the intermediate layer 65d of the next downstream hierarchy of the branch network 62. In the intermediate layer 65d, the feature map having the plurality of channels is generated by performing the deconvolution processing using the plurality of kernels on the feature map passed from the intermediate layer 65c of the upstream hierarchy.

In the feature map output by the intermediate layer 65d, which is the intermediate layer on the most downstream side of the branch network 62, the number of elements of the convolution result is 1024, 1024, and 3. Accordingly, the YUV image having 1024×1024 pixels in the vertical and horizontal directions, which consists of three channels of the Y image, the U image, and the V image, can be obtained. In this way, the branch network 62 generates the sub-prediction brightness signal image 64, which is the Y image having 1024×1024 pixels in the vertical and horizontal directions.

The loss value is calculated by comparing the prediction brightness signal image 33 and the sub-prediction brightness signal image 64 with the Y image of the source image 63b, which is the teacher data, in the comparison unit 52a and the comparison unit 52b, respectively. The loss value is a value calculated by a loss function, and is a value which evaluates how much the prediction brightness signal image 33 and the sub-prediction brightness signal image 64 can correctly restore the source image 63 in a case in which the prediction brightness signal image 33 and the sub-prediction brightness signal image 64 are compared with the source image 63.

As the loss function, a loss function used for the super-resolution, the CNN, or the like can be adopted, and a precision ratio, a reproducibility rate, an F-number (Dice coefficient), an IoU (Jaccard coefficient), a sum-of-squares error, an intersection entropy error, and the like can be adopted. Which loss function is used may be determined by using the evaluation indexes related to two or more loss values in a case in which two or more loss values different from each other are calculated by using loss functions different from each other and then the training is performed by using each of the loss functions.

It should be noted that, since the prediction brightness signal image 33 and the sub-prediction brightness signal image 64, which are the super-resolution images, may have a higher resolution than the Y image of the source image 63b before the deterioration processing, in addition to using the loss value having the minimum value in a case in which the prediction brightness signal image 33 and the sub-prediction brightness signal image 64 are the same as the Y image of the source image 63b before the deterioration processing for each pixel, the loss value in which the loss value is minimized in a case in which the prediction brightness signal image 33 and the sub-prediction brightness signal image 64 have a higher resolution than the Y image of the source image 63b before the deterioration processing may be calculated. Specifically, by adopting the technique of unsupervised learning, such as the GAN, it may be possible to calculate the loss value in which the loss value is minimized in a case in which the prediction brightness signal image 33 and the sub-prediction brightness signal image 64 have a higher resolution than the Y image of the source image 63b before the deterioration processing.

The feedback controller 53 uses the two loss values calculated by the comparison unit 52a and the comparison unit 52b to update the parameters and the like in the learning model 61 such that the prediction brightness signal image 33 and the sub-prediction brightness signal image 64 have a higher resolution than the Y image of the source image 63b before the deterioration processing to adjust the adjustment items. The feedback controller 53 can adjust the parameters and the like such that the two loss values are minimized.

Further, in the prediction brightness signal generation model 41, it is preferable that the prediction brightness signal image 33 and the sub-prediction brightness signal image 64 have a higher resolution than the Y image of the source image 63b before the deterioration processing. Therefore, in the control by the feedback controller 53, the parameters and the like may be adjusted with a goal of not minimizing the loss value, that is, the parameters and the like may be adjusted by setting a specific loss value in a case in which the prediction brightness signal image 33 and the sub-prediction brightness signal image 64, which are the super-resolution images, have a higher resolution than the Y image of the source image 63b before the deterioration processing in the prediction brightness signal image 33 and the sub-prediction brightness signal image 64, which are the super-resolution images, and the Y image of the source image 63b before the deterioration processing, and using the specific loss value as a goal.

In the training, these series of flows using the source image 63 are repeatedly performed by using a plurality of source images 63. The training is completed in a case in which the parameters and the like are adjusted such that the output prediction brightness signal image 33 and sub-prediction brightness signal image 64 have a resolution which is the same as or higher than the resolution of the Y image of the source image 63b before the deterioration processing, and it is evaluated that the results of the output prediction brightness signal image 33 and sub-prediction brightness signal image 64 are not improved even in a case in which the training is further performed. The loss function or the like described above can be used for the evaluation. The image processing unit 12 uses the prediction brightness signal generation model 41 in this case in which the parameters and the like are adjusted, as the trained model.

It should be noted that, in the prediction brightness signal generation model 41 (see FIG. 4), the input yuv image 32 including the y image 32a, the u image 32b, and the v image 32c is used as the input, and as a result of the super-resolution processing, the super-resolution YUV image 47 including the Y image 33a, the U image 33b, and the V image 33c is obtained. However, only the Y image 33a, which is the brightness signal image, is used to calculate the loss and to perform the feedback. As described above, in the prediction brightness signal generation model 41, it is preferable to perform the super-resolution processing once on the input yuv image 32 including the brightness signal image and the color difference signal image. That is, although only the brightness signal image, such as the Y image 33a, is used to calculate the loss value and to update the parameters, the color difference signal image other than the y image 32a is also input to the prediction brightness signal generation model 41, and the processing of outputting the super-resolution images thereof is performed. The reason is that the super-resolution image of the brightness signal image can be generated in a state in which the information amount is larger.

In addition, as described above, in the present embodiment, networks of the prediction brightness signal generation model 41 and the branch network 62, which are two networks different from each other and generate two training prediction brightness signal images different from each other, respectively, by the super-resolution processing are provided. Then, by using the prediction brightness signal image 33 and the sub-prediction brightness signal image 64, which are the training prediction brightness signal images obtained by these two networks, respectively, the comparison unit 52 obtains the two loss values. Then, the parameters of the prediction brightness signal generation model 41 are updated by using these two loss values.

In addition, in the above description, the case is described in which the learning model 61 including the plurality of parameters set in advance and the like is trained. However, the trained model including the plurality of parameters may be trained again after the training is completed. The training in this case is the same as a case in which the learning model 61 is trained as described above.

Further, in the above description, in the information amount decrease processing in the folded layer 44, the information amount decrease is evaluated based on the number of elements. However, the decrease of the information amount may be evaluated based on the number of bits of the entire image or feature map. That is, the information amount decrease processing need only be any processing as long as the number of bits is decreased. Further, regarding the number of bits in the prediction brightness signal generation model 41 (see FIG. 4), it is preferable to decrease the information amount in the folded layer 44 such that the information amount is smaller than the information amount in the input yuv image 32 input to the prediction brightness signal generation model 41.

Figure 8:
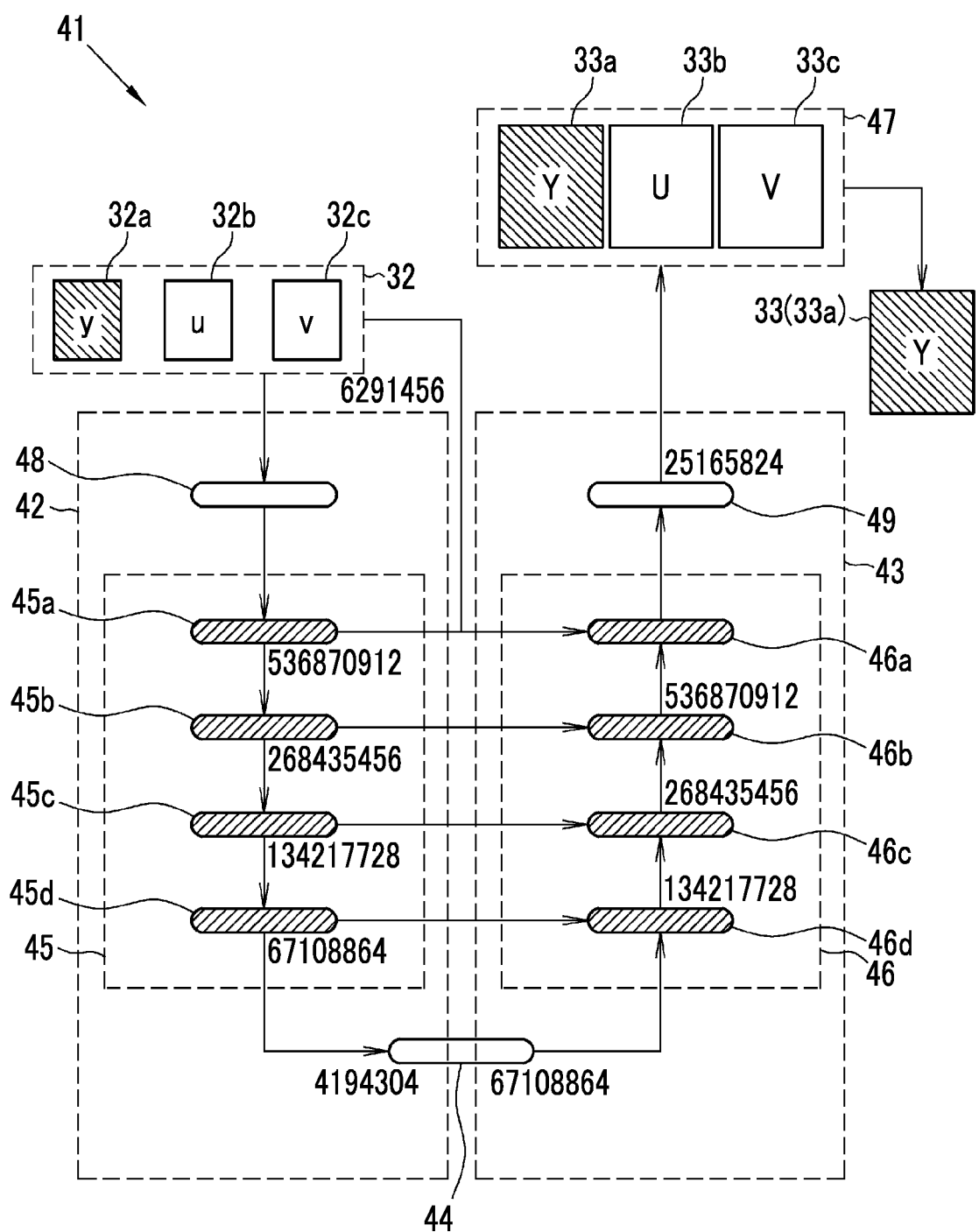
FIG. 8 is an explanatory diagram showing a flow of processing of the prediction brightness signal generation model showing the number of bits.

FIG. 8 shows a numerical character of the number of bits instead of the number of elements in FIG. 4. In the present embodiment, the information amount of the input yuv image 32 is 6291456 bits because the number of elements is 5125123 and the data type is an integer type of 8 bits, whereas the information amount is 4194304 bits because the data type is converted into the floating point constant type by the input layer 48 and the number of elements in the first half of the folded layer 44 is 32, 32, and 128. In the information amount decrease processing in the folded layer 44, any means other than the decrease of the number of elements that can decrease the information amount represented by the number of bits can be appropriately used.

Figure 9:
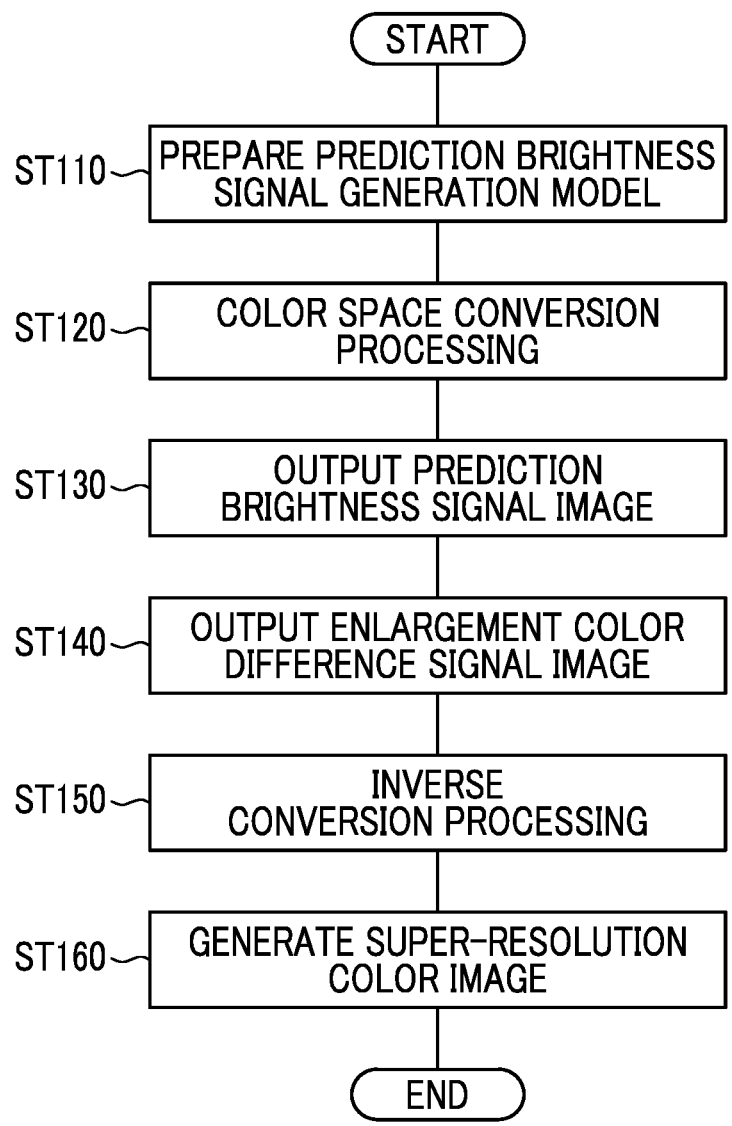
FIG. 9 is a flowchart showing a flow of processing of the image processing unit.

A flow of processing of generating the super-resolution image by performing the super-resolution processing by the image processing apparatus 10 will be described. As shown in FIG. 9, the image processing unit 12 prepares the prediction brightness signal generation model 41, which is the trained model, generated by training the learning model 61 such that the super-resolution processing can be suitably performed (step ST110). The input rgb image 31 which is the target of the super-resolution processing is prepared by using the prediction brightness signal generation model 41, and the color space conversion processing is performed by the color space conversion unit 21 (step ST120).

The input yuv image 32 generated by the color space conversion processing is processed by the image processing unit 12. By inputting the input yuv image 32 to the input layer 48 of the encoder 42 of the prediction brightness signal generation model 41, the prediction brightness signal generation model 41 performs the processing on the input yuv image 32 and outputs the prediction brightness signal image 33 based on the input yuv image 32 (step ST130).

In addition, the enlargement image generation unit 23 outputs the enlargement color difference signal image 34 based on the input yuv image 32 (step ST140). The color space inverse conversion unit 24 acquires the prediction brightness signal image 33 and the enlargement color difference signal image 34, and performs the inverse conversion processing on the prediction brightness signal image 33 and the enlargement color difference signal image 34 (step ST150). The super-resolution RGB image 35 is generated by the inverse conversion processing (step ST160).

In the CNN, the downsampling is often performed by using max pooling or the convolution processing, and the feature amount is extracted while decreasing the resolution. In this case, it is common to increase the number of channels such that the information amount can be maintained, and the feature amount output from the intermediate layer often maintains the information redundantly. Even in the super-resolution using the CNN, the encoder maintains the information amount by increasing the number of channels instead of decreasing the resolution. Maintaining the information amount of the input image that is closest to the original image, which is the source image, and accurately maintains the information is a shortcut for generating the super-resolution image. However, as a result, the feature extraction by the encoder is limited to the extraction of the feature for correcting the input image to the original image, and it is difficult to exceed the image quality of the original image.

Therefore, in the learning model 61, the information amount is decreased in the folded layer 44, which is the final layer of the encoder 42, such that more features of the image can be extracted by the encoder 42. Further, the independent branch network 62 that generates the super-resolution and is branched from the folded layer 44 is connected. The branch network 62 is used only during the training. The decrease of the information amount in the folded layer 44 is implemented, for example, by adjusting the number of channels. Adjusting the number of channels is to adjust the number of elements, as described above. Further, as described above, in the input yuv image 32, which is the input image, has the resolution of 512×512, has three channels of yuv, and is an integer type 8-bit image, the information amount is 6291456 bits. In the folded layer 44, the resolution is downsampled to 32×32 in the vertical×horizontal direction. Therefore, by setting the number of channels to 128, the information amount is decreased by 2097062 bits to be 4194394 bits.

The independent branch network 62 is required to generate the original image based on the decreased information amount. Therefore, in the training, the independent branch network 62 can work to enable the extraction of more emphasized and important image features. In addition, in the decreased information, the feature map, which is the feature amount output from the encoder 42 of the U-Net, is shared by the decoder 43, so that the information amount is maintained.

Therefore, in the learning model 61 and the prediction brightness signal generation model 41 obtained by training the learning model 61, it is possible to generate the super-resolution image in which the image qualities, such as the resolution and the sense of resolution, are improved. With the configuration described above, the super-resolution image can be made to an image having a higher image quality than the source image 63 before the deterioration processing.

Figure 10:
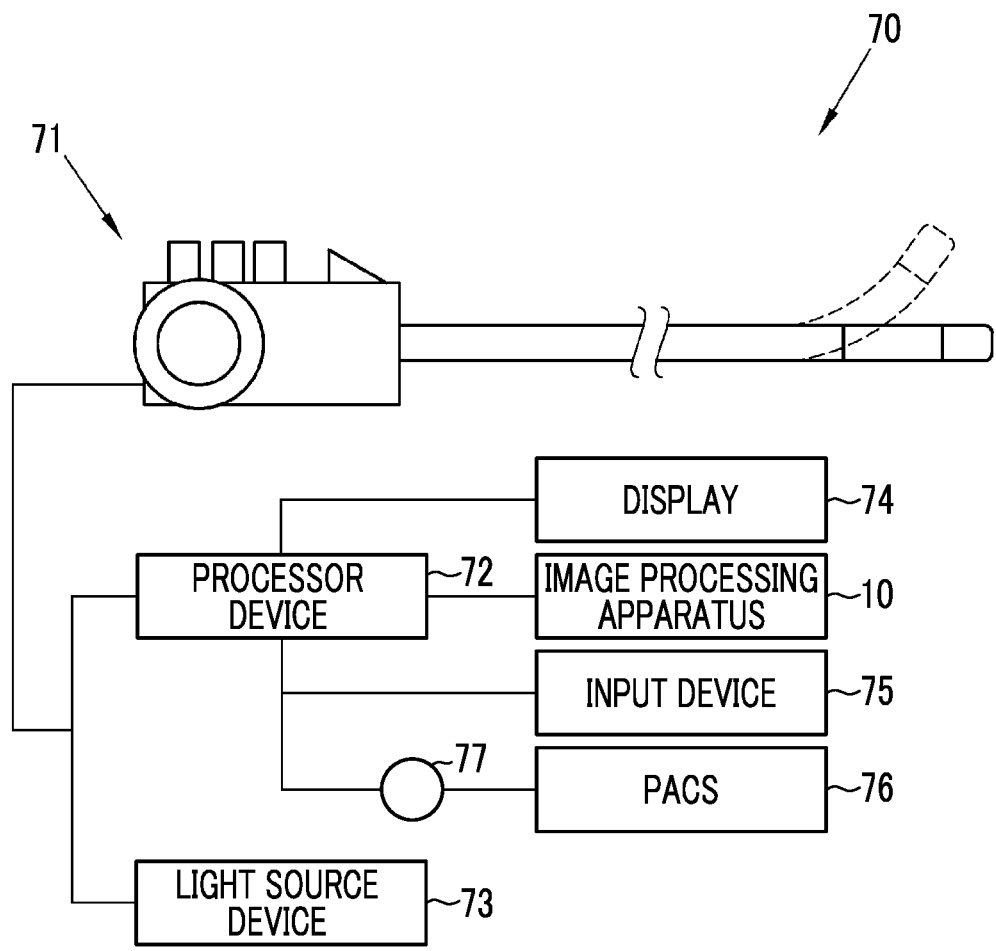
FIG. 10 is a schematic diagram of an endoscope system.

The image processing apparatus 10 may acquire an endoscope image captured by using the endoscope as the color image. As shown in FIG. 10, the endoscope system 70 comprises an endoscope 71 that images the subject to generate the endoscope image, a processor device 72 that performs control of the endoscope 71, a light source device 73, and the like, the light source device 73 that emits illumination light for irradiating the subject from a distal end part of the endoscope 71, a display 74 that displays the endoscope image or the like, and an input device 75, such as a touch panel, a keyboard, or a mouse, which is used to input information to the processor device 72. In addition, the processor device 72 is connected to a picture archiving and communication system (PACS) 76 that stores and manages a medical image, such as the endoscope image acquired by the endoscope, via a network 77.

Figure 11:
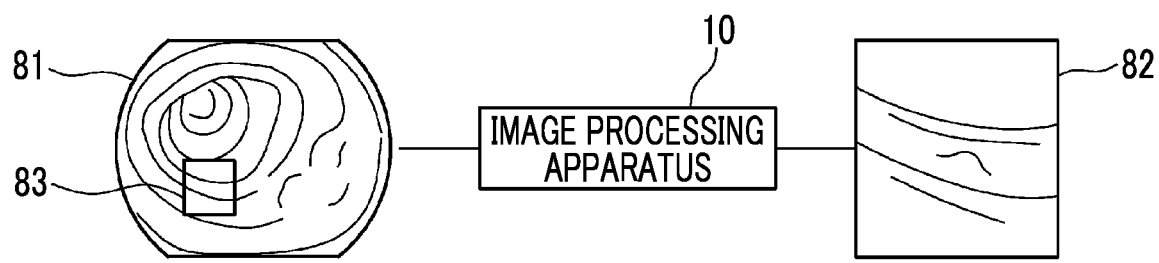
FIG. 11 is an explanatory diagram showing generation of a super-resolution endoscope image.

As shown in FIG. 11, in the endoscope system 70, the image processing apparatus 10 is an apparatus that receives an endoscope image 81 acquired by the endoscope 71 from the processor device 72 or the PACS 76, and generates a super-resolution endoscope image 82 in which the resolution of the received endoscope image 81 is increased. The super-resolution endoscope image 82 is an image obtained by performing the super-resolution processing on the endoscope image 81 by the image processing apparatus 10. In the present embodiment, the super-resolution processing is performed on a partial endoscope image 83 in which a part of the endoscope image 81 is cut out. The setting of the partial endoscope image 83 may be performed by a user of the endoscope system 70, or may be performed by the image processing apparatus 10 or the like. The super-resolution endoscope image 82 of the generated partial endoscope image 83 may be displayed on the display 74 via the processor device 72 or stored in the PACS 76 via the network 77.

Since the endoscope system 70 is configured as described above, the super-resolution endoscope image 82 of the endoscope image 81 can be generated and displayed on the display 74 or stored in the PACS 76 via the network 77.

Figure 12:
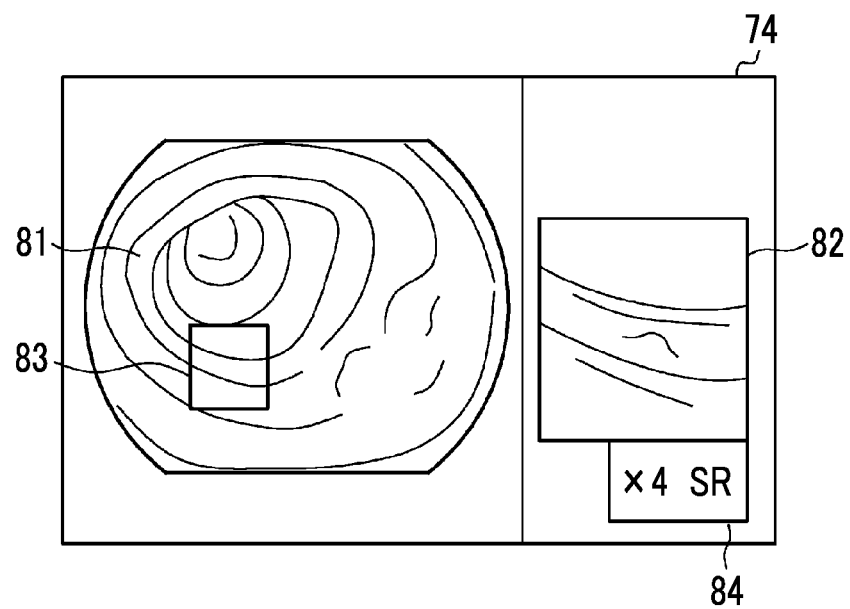
FIG. 12 is an image diagram showing the super-resolution endoscope image and an indicator displayed on a display.

It should be noted that, as shown in FIG. 12, in a case in which the super-resolution endoscope image 82 is displayed on the display 74, it is preferable to display, on the display 74, the super-resolution endoscope image 82 and an indicator 84 indicating that the displayed image is the super-resolution endoscope image 82. The indicator 84 need only be displayed in such a manner that the user can understand that the image displayed on the display 74 is the super-resolution endoscope image 82, and may display "×4" indicating, as a numerical value of magnification, how many times the super-resolution endoscope image 82 is enlarged as compared with the input endoscope image 81 and a character "SR" indicating that the image is the super-resolution image, as shown in FIG. 12.

In the endoscope system 70, the image processing apparatus 10 is incorporated to generate the enlargement image of the endoscope image and display the generated enlargement image on the display 74, whereby the super-resolution endoscope image 82 in a state of high resolution can be used as a reference for diagnosis by the doctor or the like. The endoscope image has the feature that a large amount of red is contained as a color and there are not so many other colors. In this case, the image processing apparatus 10 performs the color space conversion on the brightness signal image and the color difference signal image, and generates the super-resolution endoscope image 82 by using the image in which the super-resolution processing is performed only on the brightness signal image, so that it is possible to generate a preferable super-resolution image in which the resolution is excellent and the noise is decreased in the generated super-resolution endoscope image 82. Therefore, the image processing apparatus 10 can be suitably used for the super-resolution processing of the endoscope image.

It should be noted that each of the functional configuration units described above is implemented as the program that causes the computer to function. Therefore, the image processing program according to the embodiment of the present invention causes the computer to execute the function of acquiring the color image including the plurality of primary color signals, the function of performing the color space conversion processing on the color image to generate the brightness signal image and the color difference signal image, the function of performing the super-resolution processing on the brightness signal image to generate the prediction brightness signal image, and the function of using the prediction brightness signal image to generate the super-resolution color image in which the resolution of the color image is increased.

In the embodiment described above, a hardware structure of a processing unit that executes various types of processing, such as the image acquisition unit 11, the image processing unit 12, the output unit 13, the learning unit 14, and the like provided in the image processing apparatus 10 or the processor device 72 is various processors as described below. Examples of the various processors include a central processing unit (CPU), which is a general-purpose processor that executes software (program) to function as various processing units, a programmable logic device (PLD), which is a processor of which a circuit configuration can be changed after manufacturing, such as a field programmable gate array (FPGA), and a dedicated electric circuit, which is a processor of which a circuit configuration is designed exclusively for executing various types of processing.

One processing unit may be configured by using one of these various processors, or may be configured by using a combination of two or more same type or different type of processors (for example, a plurality of FPGAs, or a combination of a CPU and an FPGA). In addition, a plurality of the processing units may be configured by using one processor. As an example in which the plurality of processing units are configured by using one processor, first, there is a form in which one processor is configured by using a combination of one or more CPUs and software, and this processor functions as the plurality of processing units, as represented by a computer, such as a client or a server. Second, there is a form in which a processor, which implements the functions of the entire system including the plurality of processing units with one integrated circuit (IC) chip, is used, as represented by a system on chip (SoC) or the like. As described above, various processing units are configured by using one or more of the various processors described above, as the hardware structure.

Further, the hardware structure of these various processors is, more specifically, an electric circuit (circuitry) having a form in which circuit elements, such as semiconductor elements, are combined.

EXPLANATION OF REFERENCES

10: image processing apparatus
11: image acquisition unit
12: image processing unit
13: output unit
14: learning unit
21: color space conversion unit
22: prediction brightness signal generation unit
23: enlargement image generation unit
24: color space inverse conversion unit
31: input rgb image
31a: r image
31b: g image
31c: b image
32: input yuv image
32a: y image
32b: u image
32c: v image
33: prediction brightness signal image
33a: Y image
33b: U image
33c: V image
34: enlargement color difference signal image
34a: U image
34b: V image
35: super-resolution RGB image
35a: super-resolution R image
35b: super-resolution G image
35c: super-resolution B image
41: prediction brightness signal generation model
42: encoder
43: decoder
44: folded layer
45, 45a, 45b, 45c, 45d: intermediate layer
46, 46a, 46b, 46c, 46d: intermediate layer
47: super-resolution YUV image
48: input layer
49: output layer
51: deterioration processing unit
52, 52a, 52b: comparison unit
53: feedback controller
61: learning model
62: branch network
63, 63a, 63b: source image
64: sub-prediction brightness signal image
70: endoscope system
71: endoscope
72: processor device
73: light source device
74: display
75: input device 76: PACS
77: network
81: endoscope image
82: super-resolution endoscope image
83: partial endoscope image
84: indicator

What is claimed is:

1. An image processing apparatus comprising:
a processor configured to:
   acquire a color image including a plurality of primary color signals;
   perform color space conversion processing on the color image to generate a brightness signal image and a color difference signal image;
   perform super-resolution processing on the brightness signal image and the color difference signal image to generate a prediction brightness signal image; and
   use the prediction brightness signal image to generate a super-resolution color image in which a resolution of the color image is increased.

2. The image processing apparatus according to claim 1, wherein the processor is configured to:
   perform enlargement processing, which is different from the super-resolution processing, on the color difference signal image to generate an enlargement color difference signal image; and
   perform inverse conversion processing on the prediction brightness signal image and the enlargement color difference signal image to generate the super-resolution color image.

3. The image processing apparatus according to claim 2, wherein the enlargement processing is simple enlargement processing or upsampling processing.

4. The image processing apparatus according to claim 1, wherein the super-resolution processing is processing using a convolutional neural network.

5. The image processing apparatus according to claim 1, wherein the super-resolution processing includes upsampling processing or deconvolution processing.

6. The image processing apparatus according to claim 5, wherein the super-resolution processing is processing using a U-Net.

7. The image processing apparatus according to claim 1, wherein the processor is configured to:
   include a trained model; and
   perform the super-resolution processing by the trained model.

8. The image processing apparatus according to claim 7, wherein the processor is configured to include a learning model,
the learning model includes a plurality of parameters set in advance,
the plurality of parameters are updated to generate the trained model,
the plurality of parameters are updated by using a loss value, and
the loss value is obtained by:
   performing the color space conversion processing on a training image including the plurality of primary color signals to generate a color conversion image;
   performing deterioration processing on the color conversion image to generate a training brightness signal image; and
   comparing a training prediction brightness signal image with the training image, the training prediction brightness signal image being generated by performing the super-resolution processing based on the training brightness signal image.

9. The image processing apparatus according to claim 7, wherein the trained model includes a plurality of parameters,
the plurality of parameters are updated by using a loss value, and
the loss value is obtained by:
   performing the color space conversion processing on a training image including the plurality of primary color signals to generate a color conversion image;
   performing deterioration processing on the color conversion image to generate a training brightness signal image; and
   comparing a training prediction brightness signal image with the training image, the training prediction brightness signal image being generated by performing the super-resolution processing based on the training brightness signal image.

10. The image processing apparatus according to claim 8, further comprising:
two networks that are different from each other and perform the super-resolution processing to generate two training prediction brightness signal images different from each other, respectively,
wherein the processor is configured to:
   use the training prediction brightness signal images obtained by the two networks, respectively, to obtain two loss values; and
   use the two loss values to update the plurality of parameters.

11. The image processing apparatus according to claim 1, wherein the processor is configured to perform the super-resolution processing once on a processed image including the brightness signal image and the color difference signal image.

12. The image processing apparatus according to claim 1, wherein an endoscope image captured by using an endoscope is acquired as the color image.

13. An image processing method comprising:
a step of acquiring a color image including a plurality of primary color signals;
a step of performing color space conversion processing on the color image to generate a brightness signal image and a color difference signal image;
a step of performing super-resolution processing on the brightness signal image to generate a prediction brightness signal image; and
a step of using the prediction brightness signal image to generate a super-resolution color image in which a resolution of the color image is increased.

14. A non-transitory computer readable medium for storing a computer-executable program for causing a computer to function as an image processing apparatus, the computer-executable program causing the computer to execute:
a function of acquiring a color image including a plurality of primary color signals;
a function of performing color space conversion processing on the color image to generate a brightness signal image and a color difference signal image;
a function of performing super-resolution processing on the brightness signal image to generate a prediction brightness signal image; and
a function of using the prediction brightness signal image to generate a super-resolution color image in which a resolution of the color image is increased.

15. An endoscope system comprising:
an endoscope that images a subject to generate an endoscope image;
a display that displays the endoscope image; and
an image processing apparatus that includes a processor and generates a super-resolution endoscope image in which a resolution of the endoscope image is increased,
wherein the processor is configured to:
  acquire the endoscope image as a color image;
  generate the super-resolution endoscope image in which the resolution of the endoscope image is increased; and
  perform control of displaying the super-resolution endoscope image on the display.

16. The endoscope system according to claim 15, wherein the processor is configured to display the super-resolution endoscope image on the display, and display an indicator indicating that a displayed image is the super-resolution endoscope image.

17. The endoscope system according to claim 15, wherein the image processing apparatus is the image processing apparatus according to claim 1.

\* \* \* \* \*